US00PP35961P2

(12) United States Plant Patent
Hansen

(10) Patent No.: US PP35,961 P2
(45) Date of Patent: Jul. 2, 2024

(54) ***COREOPSIS* PLANT NAMED 'Scarlet Ribbons'**

(50) Latin Name: *Coreopsis verticillata*
Varietal Denomination: Scarlet Ribbons

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 18/445,664

(22) Filed: Dec. 15, 2023

(51) Int. Cl.
*A01H 5/02* (2018.01)
*A01H 6/14* (2018.01)

(52) U.S. Cl.
USPC ..... Plt./417
CPC ..... *A01H 6/14* (2018.05)

(58) Field of Classification Search
USPC ..... Plt./417
CPC ..... A01H 6/14; A01H 5/02
See application file for complete search history.

*Primary Examiner* — Keith O. Robinson

(57) ABSTRACT

A new and distinct Threadleaf *Coreopsis* plant, *Coreopsis verticillata* plant named 'Scarlet Ribbons', with narrowly-linear, deeply-dissected, typically 3 to 5-lobed foliage of bright-green, numerous flowers of velvety maroon-red ray florets with deep maroon disk florets are produced over a prolonged flowering season from mid-June until late summer. The new plant is useful for landscaping as a specimen plant, en masse, in containers, and as a cut flower.

1 Drawing Sheet

Botanical designation: *Coreopsis verticillata.*
Cultivar denomination: 'Scarlet Ribbons'.

STATEMENT REGARDING PRIOR DISCLOSURES UNDER 37 CFR 1.77(B)(6)

The first public disclosure of 'Scarlet Ribbons', in the form of a website to the public and email release to customers, was made by Walters Gardens, Inc. on Dec. 1, 2023. Walters Gardens, Inc. obtained the new plant and information about the new plant directly from the inventor. The first offer for sale of the new plant was on Jan. 9, 2023, by Walters Gardens, Inc. No plants of *Coreopsis* 'Scarlet Ribbons' have been offered for sale or sold, in this country or anywhere in the world, nor has any disclosure of the new plant been made, more than one year prior to the filing date of this application, and such sale or disclosure within one year was either derived directly or indirectly from the inventor.

BACKGROUND OF THE PLANT

The present invention relates to the new and distinct Threadleaf *Coreopsis* herein also referred to as *Coreopsis* 'Scarlet Ribbons', by the cultivar name, 'Scarlet Ribbons', or as the new plant. The new plant was a cross by the inventor on Aug. 1, 2018, between the proprietary unreleased hybrid identified by breeder code 17-10-1 (not patented) crossed with the proprietary unreleased hybrid identified by breeder code 17-11-xx (not patented) at the research facility of a wholesale perennial nursery based in Zeeland, MI, USA. The single seedling selected by breeder code and identified as 18-65-3 was then isolated and compared in subsequent years to other *Coreopsis* and subsequently found to be different from all cultivars known to the discoverer.

Asexual propagation at the same nursery in Zeeland, MI, USA by cuttings has shown 'Scarlet Ribbons' to be stable and reproduce true to type in successive generations since spring 2019.

SUMMARY OF THE PLANT

*Coreopsis* 'Scarlet Ribbons' has not been observed in all possible environmental conditions. The phenotype may vary slightly with changes in environments such as light intensity, fertility, water availability, etc. without however, any variations in genotype.

*Coreopsis* 'Scarlet Ribbons' is distinct from all cultivars known to the inventor in the following traits:

1. Narrow foliage with compact height and dense habit.
2. Heavy flowering of velvety maroon-red ray florets with deep maroon centers.
3. Flowers produced tightly and densely above the bright-green thin foliage.
4. Long flowering period beginning with concentration in mid-June and continuing until late summer.

Plants of *Coreopsis* 'Scarlet Ribbons' are most similar to: 'Red Satin' U.S. Plant Pat. No. 25,736, 'Limerock Ruby' U.S. Plant Pat. No. 15,455, 'Mercury Rising' U.S. Plant Pat. No. 24,689, 'Broad Street' U.S. Plant Pat. No. 24,598, 'Hot Paprika' U.S. Plant Pat. No. 28,522, 'Red Elf' U.S. Plant Pat. No. 27,918, and 'Red Chiffon' U.S. Plant Pat. No. 27,528.

'Red Satin' has ray florets that are dark red toward the center and brilliant yellow toward the apices and the foliage is more divided and more oblanceolate. 'Limerock Ruby' is winter hardy only to USDA zone 8, has ray florets that are deep crimson red, and the foliage is not as dissected. 'Mercury Rising' has a taller habit with ray florets that are dark red proximally and white tips in high temperatures. 'Broad Street' has a taller habit, lighter reddish ray florets flecks of yellow toward the apices. 'Hot Paprika' has deep red ray florets. 'Red Elf' has a shorter habit, burgundy-red ray florets with bright yellow center disks. 'Red Chiffon' has ray florets that are also paler yellow on the outside and not as dark burgundy on the inside, and the flowers produce no seed.

The female has ray florets that are near white toward the apices and reddish in the proximal portion. The male parent has ray florets that are nearly all burgundy with a small amount of yellow near the apices.

BRIEF DESCRIPTION OF THE DRAWINGS

The color drawings illustrate the overall characteristics of *Coreopsis* 'Scarlet Ribbons' as three-year-old plants grown in full-sun in Zeeland, Michigan. The colors are as true as reasonably possible given the technology available. The color values may vary slightly depending on light intensity and quality.

DETAILED BOTANICAL DESCRIPTION

Figure 1:
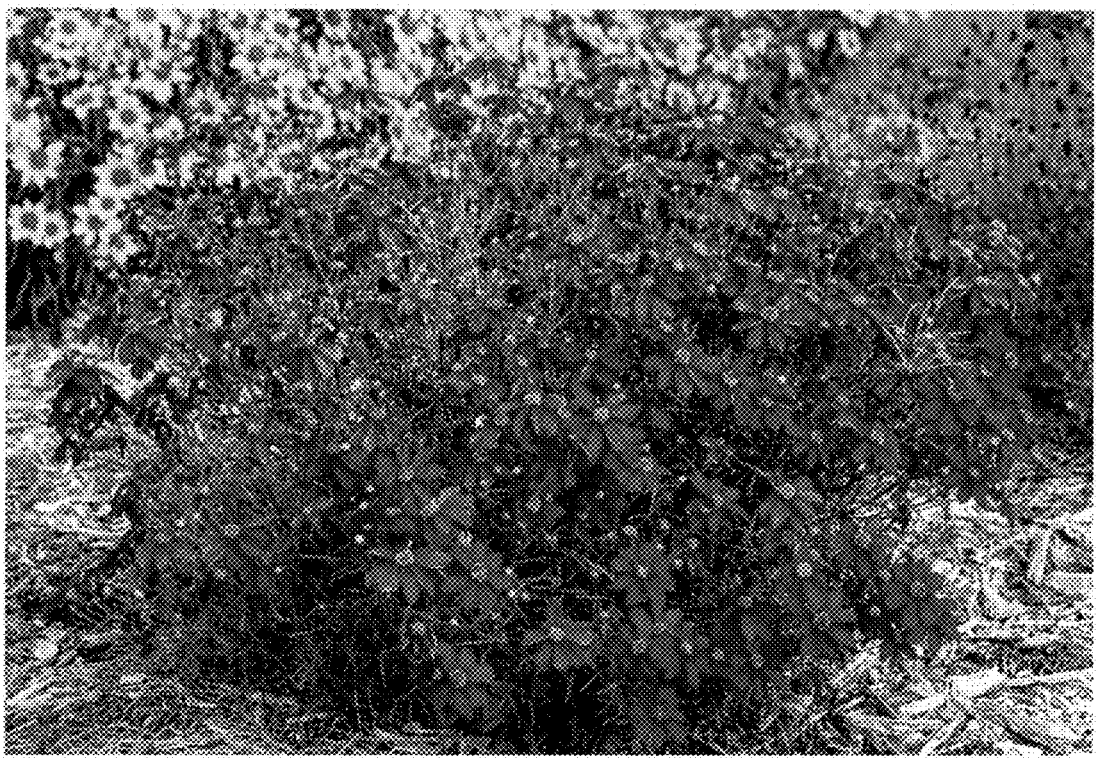
FIG. 1 shows a new plant in a landscape environment.
Figure 2:
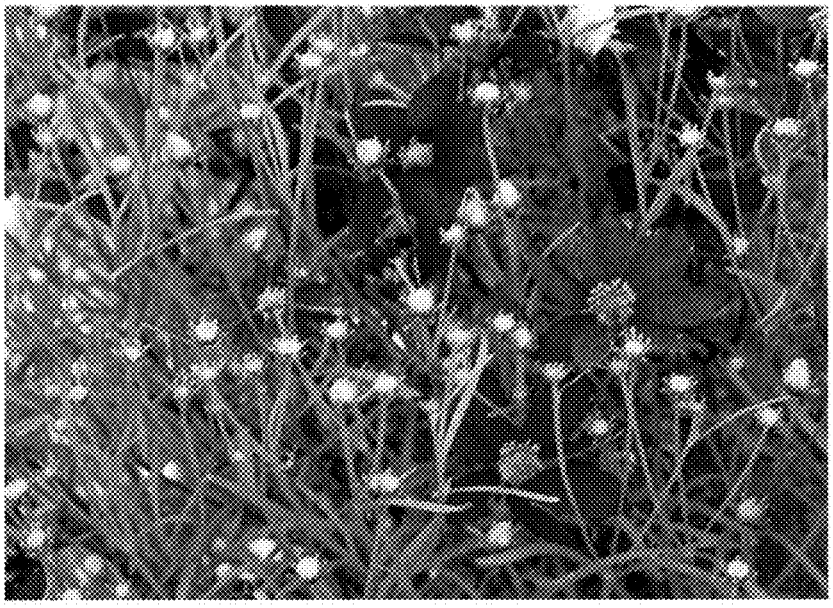
FIG. 2 shows a close-up of the flowers, buds, and thin foliage of the new plant.

The following description is based on a three-year-old plant growing in a full-sun trial garden and two-year-old plants growing in a partially shaded greenhouse in Zeeland, MI, USA. Environmental conditions for the growing season daytime temperatures range between 12-30° C., and night temperatures range between 6-19° C. Except for ordinary dictionary color usage, color references are according to The Royal Horticultural Society Colour Chart, 2015 edition.

Parentage: The female or seed parent is the proprietary hybrid 17-10-1; the male or pollen parent is the proprietary hybrid 17-11-xx;

Asexual propagation: Cuttings, about 10 to 14 days to initiate roots; time to finish as #1 field grown size about 9 months;

Plant habit: Dense axillary branches; rounded, herbaceous perennial mound; up to 42 cm wide and 30 cm tall; average about 40 cm across and 29 cm tall;

Branches: Up to 12 per stem, lower branches compound; glabrous, cylindrical; to 20 cm long and 2 mm diameter; emerging at an angle about 45 degrees above horizontal;

Branch color: Nearest RHS 137B;

Leaves: Opposite; entire; variable, linear to irregularly tri-lobed or penta-lobed, deeply dissected to midrib; acute apex; base attenuate; sessile; glabrous;

Leaf size: Up to 5.5 cm long and 5.2 cm wide with segments about 3 mm wide, average about 4 cm long and 3.5 cm wide; side lobes at about a 45° to 60° angle to center lobe; center lobe to 3.5 cm long and 2 mm wide;

Leaf color: Young expanding leaves adaxial and abaxial nearest RHS 146B; mature leaves adaxial between RHS NN137A and RHS NN137B, abaxial between RHS 137A and RHS NN137B;

Veins: Pinnate; only abaxial midrib obvious;

Abaxial midrib color: Adaxial nearest RHS 137A, abaxial nearest RHS 137A;

Inflorescence: Radiate; composite consisting of ray and disk florets; on terminal branches; about 4.3 cm diameter, about 1 cm tall from lower involucral bracts to top of disk florets; attitude upright to outwardly; to about 100 inflorescences per stem;

Flower fragrance: Not detected;

Phyllary: Two distinct whorls; an outer or lower set consisting of about eight, salient, glabrous adaxial and abaxial, with acute apex, lanceolate, truncate base, to about 3 mm long and 1 mm wide at base; an inner or upper set pressed tight against ray florets, usually eight in number, to about 5.5 mm long and about 3 mm wide, ovate, acute apex and rounded base;

Phyllary color: Lower set between RHS NN137A and RHS 137A both adaxial and abaxial; upper set between RHS 137A and RHS 146A in the proximal and central portion of both adaxial and abaxial, marginally and distally nearest RHS N144A both adaxial and abaxial;

Flowering period: Early summer until late summer, for about 10 weeks;

Flower longevity: 4 to 6 days on the plant or as a cut flower;

Inflorescence buds: One to two days before ray floret flattening - terete; flat top and rounded base; 6 mm wide and 15 mm tall;

Inflorescence bud color: Exposed ray florets nearest RHS 160C with veins nearest RHS 187A;

Peduncle: Cylindrical; glaucous; upright attitude; thin, wiry, stiff, strong; to about 1 mm diameter at the base and about 7.7 cm long before capitulum; about 8 ray florets and 40 to 45 disk florets per peduncle;

Peduncle color: Between RHS 137A and RHS 137B;

Stem: About seven nodes, average internode spacing about 3.2 cm; spacing increasing distally;

Stem color: Proximally nearest RHS 164B striated with nearest RHS 137B, distally nearest RHS 137B;

Node: Swollen to about 5 mm across;

Node color: As surround stem, nearest RHS 137B;

Bristles: Thin; lustrous; about 6 mm long and 0.2 mm across; color nearest RHS 163B;

Ray florets: Imperfect; sterile; zygomorphic; typically, 8 per inflorescence;

Ray floret ligule: Oblong elongate; glabrous adaxial and adaxial; apex typically two-notched; margin entire; base claw, narrowly cuneate to attenuate; opening flat to form 180° angle with other ray florets; parallel-veined; to about 21 mm long and about 9 mm wide; basal corolla claw about 2 mm long and about 0.7 mm diameter;

Ray floret color: Adaxial basal 2 mm nearest RHS 151A, middle 15 mm between RHS 187A and RHS 59A, distally with variable patches of nearest RHS 4C when first flattened and lightening to nearest RHS 4D when mature; abaxial basal 2 mm nearest RHS 151A, next proximal 7 mm nearest RHS 160D with undertone of nearest RHS 187A, distal 12 mm nearest RHS 160D;

Disk florets: About 34 per capitulum; consisting of fused tepals, staminal tube and pistil; size about 6 mm long by 1 mm wide at apex and about 0.7 mm diameter at base;

*Tepals*.—Four; 3 mm long and 1 mm wide, corolla fused in the basal 2 mm, acute apex.

*Tepal color*.—Adaxial nearest RHS 187A in distal 1 mm, abaxial distal 1 mm nearest RHS 177A, and basal 1 mm nearest RHS 4D with the middle portion between RHS 151D and RHS 150D.

*Staminal tube*.—Made up of four fused stamens, about 3 mm long.

*Anther*.—About 2 mm long, nearest RHS N186A.

*Filament*.—Four; cylindrical; about 1 mm long and 0.1 mm diameter; color nearest RHS 4A.

*Pollen*.—Fine, round, closest to RHS 15A.

*Style*.—Cylindrical; about 4 mm long and 0.2 mm diameter; nearest RHS 15D.

*Stigma*.—Bifid and cochleate as it matures; about 1 mm long and 0.3 mm diameter; color nearest RHS 15B.

Seed: Has not been observed;

*Coreopsis verticillata* 'Scarlet Ribbons' is tolerant of winter temperatures as low as −20° C. and summer temperatures as high as 40° C. Once established it is also tolerant of dry summer conditions but does best with ample moisture and good drainage. It is not known to be tolerant or susceptible to diseases and pests that are common to other *Coreopsis* cultivars.

I claim:

1. A new and distinct cultivar of *Coreopsis* plant named 'Scarlet Ribbons' as described and illustrated.

* * * * *